(12) United States Patent
James et al.

(10) Patent No.: US 11,116,304 B2
(45) Date of Patent: Sep. 14, 2021

(54) ARTICULATING EAR SHIELD

(71) Applicant: Contoure, LLC, Royal Palm Beach, FL (US)

(72) Inventors: Denise James, Royal Palm Beach, FL (US); Ronald Lanclos, Royal Palm Beach, FL (US)

(73) Assignee: Contoure, LLC, Royal Palm Beach, FL (US)

(*) Notice: Subject to any disclaimer, the term of this patent is extended or adjusted under 35 U.S.C. 154(b) by 0 days.

(21) Appl. No.: 16/176,131

(22) Filed: Oct. 31, 2018

(65) Prior Publication Data

US 2020/0128942 A1 Apr. 30, 2020

(51) Int. Cl.
*A45D 44/12* (2006.01)
*A61F 11/14* (2006.01)

(52) U.S. Cl.
CPC .............. *A45D 44/12* (2013.01); *A61F 11/14* (2013.01)

(58) Field of Classification Search
CPC .......... A45D 44/12; A61F 11/14; A61F 11/06; A61F 11/00; A63B 71/10; A44C 7/004; A42B 1/06; H04R 1/10
USPC ..................................................... 2/209, 410
See application file for complete search history.

(56) References Cited

U.S. PATENT DOCUMENTS

| | | | | |
|---|---|---|---|---|
| 520,785 A * | 6/1894 | Jung | ........................ | A61F 11/06 2/209 |
| 2,148,838 A * | 2/1939 | Roos | ....................... | A45D 44/12 2/174 |
| 2,743,454 A * | 5/1956 | Woodbury | .............. | A42B 1/068 2/172 |
| 3,452,365 A | 7/1969 | Wallace | | |
| 4,277,864 A * | 7/1981 | Orson, Sr. | ............... | A44B 99/00 24/327 |
| 4,682,374 A | 7/1987 | Geiser | | |
| 4,850,055 A * | 7/1989 | Hwang | .................... | A61F 11/06 2/209 |
| 4,872,219 A | 10/1989 | Duncan | | |
| 4,916,758 A | 4/1990 | Jordan-Ross | | |
| 6,298,493 B1 | 10/2001 | Ambroise | | |
| 6,505,633 B2 | 1/2003 | Mosely | | |
| 6,625,819 B1 * | 9/2003 | Tsai | ......................... | A61F 11/14 181/129 |
| 6,708,347 B2 | 3/2004 | Brundidge | | |
| D777,989 S | 1/2017 | Gerspach | | |
| 9,591,879 B2 * | 3/2017 | Michlitsch | .............. | A41D 13/05 |
| 2002/0023285 A1 | 2/2002 | Mosely | | |
| 2009/0100558 A1 | 4/2009 | Smith | | |

(Continued)

*Primary Examiner* — Nathan E Durham
*Assistant Examiner* — Abby M Spatz
(74) *Attorney, Agent, or Firm* — The Concept Law Group, PA; Scott D. Smiley; Scott M. Garrett

(57) ABSTRACT

An ear shield includes a lateral portion and a medial portion that are configured to respectively go over the lateral and medial sides of the auricle of a wearer's ear. The lateral and medial portions are joined together by a joining portion that acts as a cantilevered spring member, allowing the distal ends of the lateral and medial portions to move with respect to each other, but which biases the lateral and medial portions to a neutral position suitable for retaining the ear shield on a person's ear. There are articulating tabs further formed at the joining portion which extend to the rear, opposite the lateral and medial portions, that allow a user to move the lateral and medial portions relative to each other.

19 Claims, 11 Drawing Sheets

(56) References Cited

U.S. PATENT DOCUMENTS

2009/0165804 A1 7/2009 Maxwell
2013/0025034 A1* 1/2013 Durocher ................ A42B 3/16
2/423

* cited by examiner

ARTICULATING EAR SHIELD

FIELD OF THE INVENTION

The present invention relates generally to hair styling accessories, and, more particularly, relates to an ear shield that covers and protects a person's ear from heat and sharp implements commonly used in styling and cutting hair.

BACKGROUND OF THE INVENTION

When styling hair it is not uncommon, despite care being taken, for a styling implement or tool to come into contact with a person's skin, ear, or other exposed region. This can result in burns from hot implements, cuts or nicks from sharp tools, and other undesired contact. The ears can be particularly susceptible to such undesired contact because they protrude from the head, and are in close proximity, if not direct contact, with a person's hair. As a result, many people feel anxiety when having their hair styled and/or cut. This is be especially true among children, which can make them uncooperative during a visit to a hair stylist or barber.

To ease anxiety and worries over potentially being injured, and to prevent actual injuries, various types of ear coverings and skin shields have been developed having varying efficacy. A common ear shield design approach is essentially an ear cup that hangs on the ear, and is made of an insulative material, such as plastic. These one-size-fits-all type of devices have to be sized large enough to fit large ears, and as such, they are less secure on smaller ears. Accordingly, these designs are inadequate because they can easily come off the ear, don't cover enough of the ear, and don't provide ventilation to allow air and sound pass through the ear shield.

Another concern with regard to exposed skin in hair styling is exposure to chemicals used in treating and coloring hair. Contact with some hair styling chemicals can cause discomfort, or even chemical burns on the skin. Again, ears, because of their location, and protrusion from the head, tend to be especially susceptible to exposure to chemicals during hair styling. In the past this has been addressed by, for example, covering the ear with petroleum jelly or similar inert protective material, the use of "hang on" ear shields, and so on. These solutions have drawbacks of falling off, being messy, and generally just an inconvenience added to the process of hair styling.

Therefore, a need exists to overcome the problems with the prior art as discussed above.

SUMMARY OF THE INVENTION

The invention provides an articulated ear shield that overcomes the hereinafore-mentioned disadvantages of the heretofore-known devices and methods of this general type and that covers a wearer's ear while being self-retaining on the wearer's ears, and which can provide air ventilation and allow a wearer to hear unobstructedly.

Some embodiments of the inventive disclosure provide an ear shield for covering an auricle of a human ear that includes a support structure including a medial portion and a lateral portion opposing each other about a joining portion positioned in the ear shield at a rear of the auricle. The lateral portion and medial portion can be configured to receive a helix and lobule of the auricle therebetween. The medial portion can extend forward from a medial side of the joining portion and define a medial plane, and can be configured to fit over a medial side of the auricle. The lateral portion can extend forward from the joining portion at a lateral side of the joining portion and define a lateral plane, and can be configured to fit over a lateral side of the auricle. The ear shield can further include a medial articulating tab that extends rearward from the medial side of the joining portion, and a lateral articulating tab that extends rearward from the lateral side of the joining portion. The joining portion can be configured to have a spring action that biases the medial portion and the lateral portion to a substantially parallel arrangement between the medial plane and the lateral plane. The ear shield can further include a pliable heat resistant cover formed over an outer surface the lateral portion and over an outer surface of the medial portion, extending outward from the lateral portion in the lateral plane around at least a portion of a perimeter of the lateral portion.

In accordance with a further feature, the ear shield can further include a plurality of openings formed through the lateral portion of the support structure and the pliable heat resistant cover over the lateral portion.

In accordance with a further feature, the pliable heat resistant cover is silicone rubber.

In accordance with a further feature, the joining portion, medial portion, lateral portion, medial articulating tab, and lateral articulating tab are integrally formed as a unitary polymeric structure.

In accordance with a further feature, the pliable heat resistant cover over the lateral portion curves inward toward the medial portion around at least a portion of a perimeter of the pliable heat resistant cover on the lateral portion.

In accordance with a further feature, the lateral portion and the pliable heat resistant cover on the lateral portion further cover an entirety of the lateral side of the auricle.

In accordance with a further feature, the pliable heat resistant cover extends over the medial articulating tab and the lateral articulating tab, and defines a void between the medial articulating tab and the lateral articulating tab, forming a vertical trough.

In accordance with a further feature, the medial portion comprises an upper lobe that extends upward and forward from the joining portion, and a lower lobe that extends downward and forward from the joining portion. The upper lobe and the lower lobe of the medial portion form a generally arcuate shape, and the lower lobe extends farther forward than the upper lobe of the medial portion. Furthermore, the lateral portion can include an upper lobe that extends upwards and forwards from the joining portion, and a lower lobe that extends downward and forward from the joining portion, and the upper lobe and the lower lobe of the lateral portion can form a generally arcuate shape, and the lower lobe can extend farther forward than the upper lobe of the lateral portion. The ear shield can further include the upper lobe of the medial portion extending above the upper lobe of the lateral portion, and the upper and lower lobes of the lateral portion both extending farther forward than the upper and lower lobes of the medial portion.

In accordance with a further feature, the ear shield can further include a tactile protrusion formed on the heat resistant pliable cover over the lateral articulating tab.

In accordance with some embodiments of the inventive disclosure, there is provided an articulating ear shield for preventing exposure of a person's ear to styling implements and chemicals that can include a support structure that has a lateral portion and a medial portion joined by a joining portion. The joining portion can act as a cantilevered spring member between the lateral portion and the medial portion. The joining portion can bias the lateral portion and the medial portion to a neutral position relative to each other, with a space between them configured to receive an auricle of a human ear. The lateral portion can be configured engage a lateral side of the auricle, and the medial portion can be configured to engage a medial side of the auricle along a helix of the auricle. The support structure can further include a lateral articulating tab extending from the joining portion at a lateral side of the joining portion in an opposite direction from which the lateral portion extends. The support structure further including a medial articulating tab extending from the joining portion at a medial side of the joining portion in an opposite direction from which the medial portion extends. The ear shield can further include a heat resistant pliable cover formed over, and which covers, an outside of the lateral portion, and an outside of the medial portion, and which extends outward around the lateral portion in a plane defined by the lateral portion, turning toward the medial side of the auricle around a portion of a perimeter of the heat resistant pliable cover around the lateral portion in a configuration to cover the helix and a lobule of the auricle.

In accordance with a further feature, the ear shield can further include a plurality of openings formed through the lateral portion of the support structure and the pliable heat resistant cover over the lateral portion.

In accordance with a further feature, the pliable heat resistant cover is silicone rubber.

In accordance with a further feature, the medial portion comprises an upper lobe that extends upward and forward from the joining portion, and a lower lobe that extends downward and forward from the joining portion. The upper lobe and the lower lobe of the medial portion form a generally arcuate shape. The lower lobe can extend farther forward than the upper lobe of the medial portion. The lateral portion can include an upper lobe that extends upward and forward from the joining portion, and a lower lobe that extends downward and forward from the joining portion. The upper lobe and the lower lobe of the lateral portion form a generally arcuate shape, and the lower lobe can extend farther forward than the upper lobe of the lateral portion. The upper lobe of the medial portion can extend above the upper lobe of the lateral portion, and the upper and lower lobes of the lateral portion can both extend farther forward than the upper and lower lobes of the medial portion.

In accordance with a further feature, the ear shield can further include a tactile protrusion formed on the heat resistant pliable cover over the lateral articulating tab.

In accordance with a further feature, the pliable heat resistant cover extends over the medial articulating tab and the lateral articulating tab, and defines a void between the medial articulating tab and the lateral articulating tab, forming a vertical trough.

In accordance with a further feature, the cover is overmolded onto the support structure.

In accordance with some embodiments of the inventive disclosure, there is provided an articulating ear shield for protecting an auricle of a human ear that includes a support structure having a lateral portion and a medial portion which are joined together at a joining portion, and spaced apart from each other in a configuration to receive the auricle between the lateral portion and the medial portion, wherein the lateral portion extends forward from the joining portion at a lateral side of the joining portion, the medial portion extends forward from the joining portion at a medial side of the joining portion. The ear shield can further include a lateral articulating tab that extends to a rear from the joining portion at the lateral side of the joining portion, and a medial articulating tab that extends to the rear from the joining portion at the medial side of the joining portion. The ear shield can further include a heat resistant pliable cover formed over, and which covers an outside of the lateral portion and an outside of the medial portion, and which extends outward around the lateral portion in a plane defined by the lateral portion, turning toward the medial side of the auricle around a portion of a perimeter of the heat resistance pliable cover around the lateral portion in a configuration to cover a helix and a lobule of the auricle. The joining portion biases the lateral portion and the medial portion to a neutral position, and urging the lateral articulating tab and the medial articulating tab together causes the joining portion to flex and causes the lateral and medial portions to move apart at an angle.

In accordance with a further feature, the medial portion includes an upper lobe that extends upward and forward from the joining portion, and a lower lobe that extends downward and forward from the joining portion. The upper lobe and the lower lobe of the medial portion form a generally arcuate shape, and wherein the lower lobe extends farther forward than the upper lobe of the medial portion. The lateral portion includes an upper lobe that extends upwards and forwards from the joining portion, and a lower lobe that extends downward and forward from the joining portion, and the upper lobe and the lower lobe of the lateral portion form a generally arcuate shape, and the lower lobe extends farther forward than the upper lobe of the lateral portion. The upper lobe of the medial portion extends above the upper lobe of the lateral portion, and the upper and lower lobes of the lateral portion both extend farther forward than the upper and lower lobes of the medial portion.

In accordance with a further feature, the ear shield can further include a plurality of openings formed through the lateral portion of the support structure and the pliable heat resistant cover over the lateral portion.

In accordance with a further feature, the pliable heat resistant cover is silicone rubber.

Although the invention is illustrated and described herein as embodied in an articulated ear shield, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the articulated ear shield. Those skilled in the art can understand the specific meanings of the above-mentioned terms in the embodiments of the present invention according to the specific circumstances

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
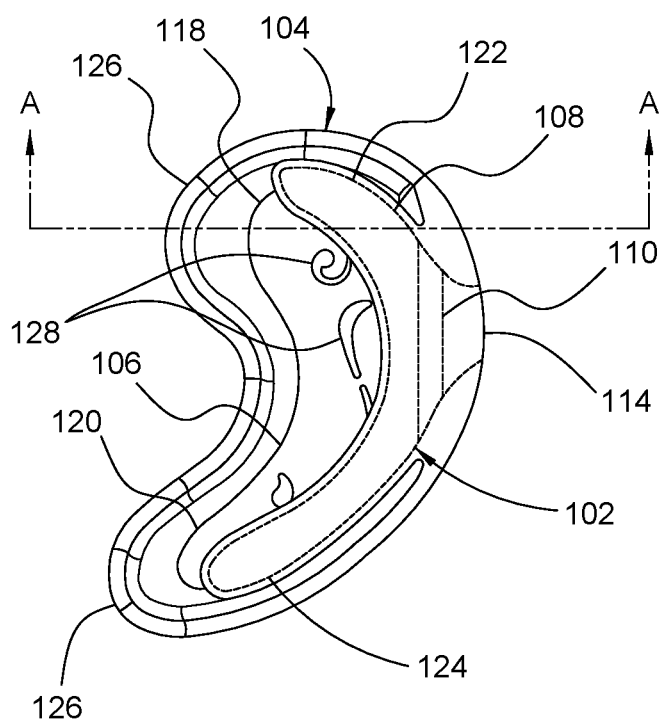
FIG. 1 is medial side elevational view of an articulated ear shield, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient articulated ear shield. Embodiments of the inventive disclosure provide an ear shield for covering an auricle of a human ear that includes a support structure including a medial portion and a lateral portion opposing each other about a joining portion positioned in the ear shield at a rear of the auricle. The lateral portion and medial portion can be configured to receive a helix and lobule of the auricle therebetween. The medial portion can extend forward from a medial side of the joining portion and define a medial plane, and can be configured to fit over a medial side of the auricle. The lateral portion can extend forward from the joining portion at a lateral side of the joining portion and define a lateral plane, and can be configured to fit over a lateral side of the auricle. The ear shield can further include a medial articulating tab that extends rearward from the medial side of the joining portion, and a lateral articulating tab that extends rearward from the lateral side of the joining portion. The joining portion can be configured to have a spring action that biases the medial portion and the lateral portion to a substantially parallel arrangement between the medial plane and the lateral plane. The ear shield can further include a pliable heat resistant cover formed over an outer surface the lateral portion and over an outer surface of the medial portion, extending outward from the lateral portion in the lateral plane around at least a portion of a perimeter of the lateral portion. The ear shield can be one of a pair of ear shields, each respectively configured to fit over the right and left ears of a person while a stylist, barber, or other person performs work on the person's hair. The ear shields can be worn in other situations as well, where the user's ears may be otherwise come into contact with sharp or hot instruments.

Figure 2:
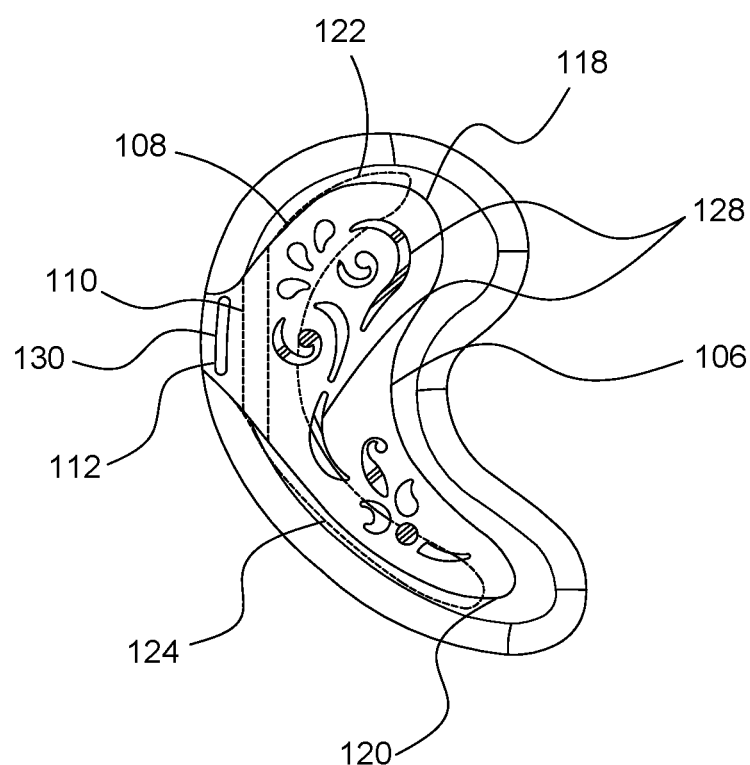
FIG. 2 is a lateral side elevational view of an articulated ear shield, in accordance with some embodiments.
Figure 3:
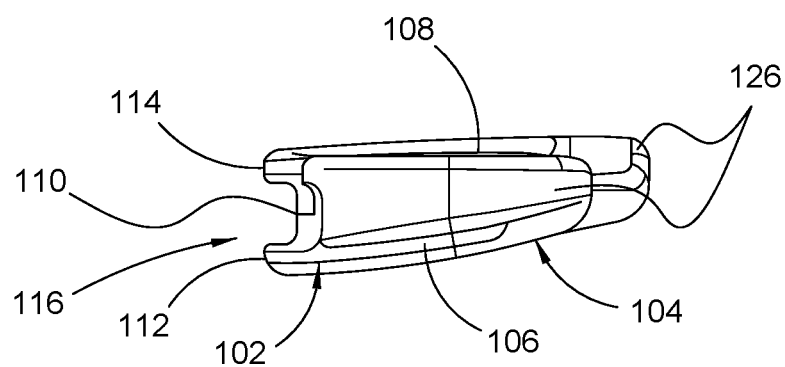
FIG. 3 is a top plan view of an articulated ear shield, in accordance with some embodiments.
Figure 4:
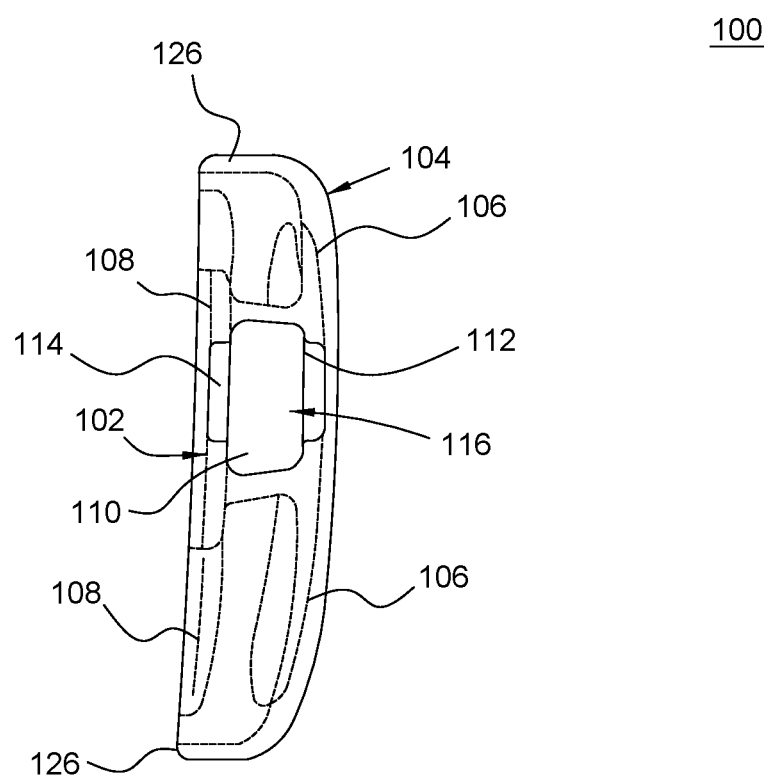
FIG. 4 is a rear elevational view of an articulated ear shield, in accordance with some embodiments.
Figure 5:
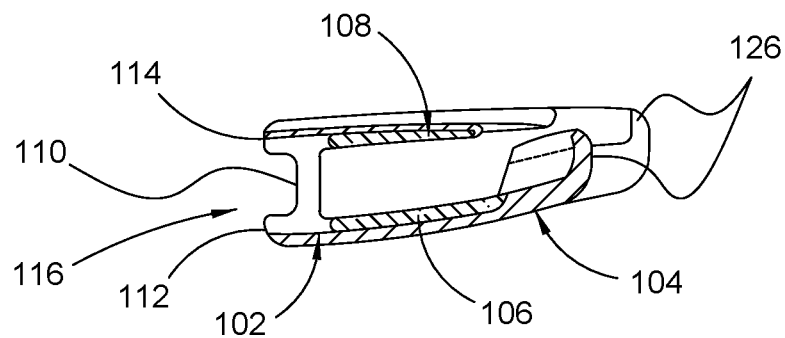
FIG. 5 is a top cutaway view of an articulated ear shield, in accordance with some embodiments.
Figure 6:
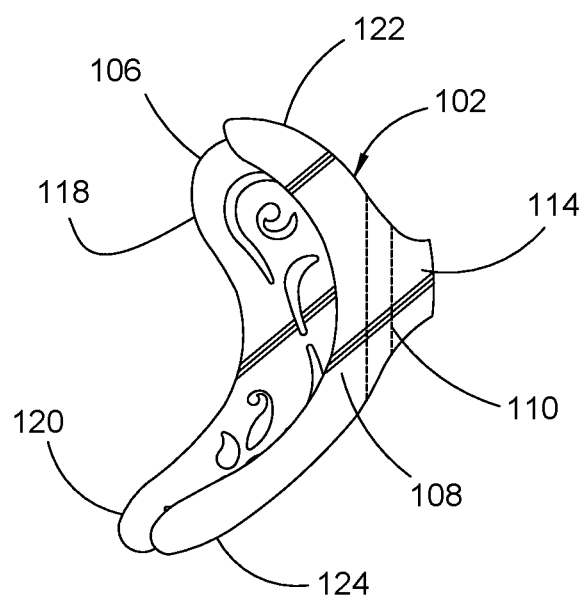
FIG. 6 is a medial side elevational view of a support structure for an articulated ear shield, in accordance with some embodiments.
Figure 7:
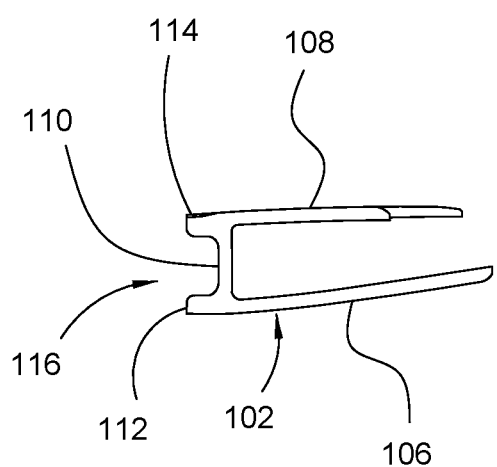
FIG. 7 is a top plan view of a support structure for an articulated ear shield, in accordance with some embodiments.
Figure 8:
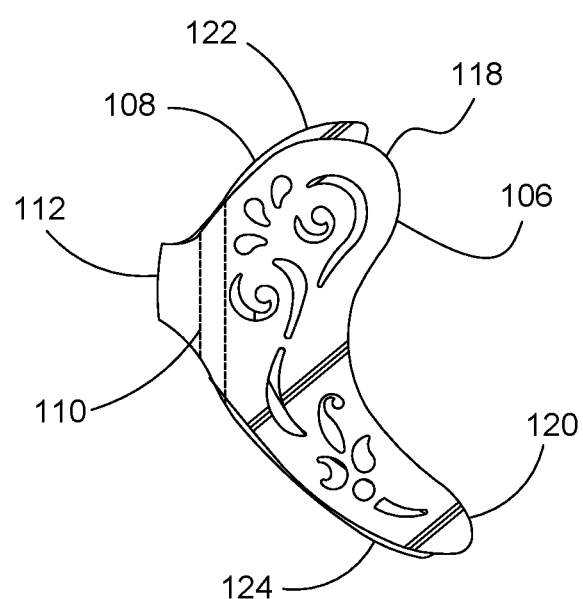
FIG. 8 is a lateral side elevational view of a support structure for an articulated ear shield, in accordance with some embodiments.

FIGS. 1-4 show various views of an exemplary articulated ear shield, in accordance with some embodiments. FIG. 1 shows a medial side elevational view, FIG. 2 shows a lateral side elevational view, FIG. 3 shows a top plan view, and FIG. 4 shows a rear elevational view of the exemplary articulated ear shield. In these and other related drawings the reference numerals are carried forward, indicating the same structure is shown from different views. FIG. 5 is a cutaway top plan view of an articulated ear shield with the cut along line AA of FIG. 1. FIGS. 6-8 show details of the support structure of an articulated ear shield as shown in FIGS. 1-5, without the cover 104. The cover 104 in FIGS. 1-4 is shown as being translucent, allowing the support structure 102 to be seen through it. In the following discussion, terms like "rear" and "rearward" refer to the direction of the back of a person's head from a given point when the articulating ear shield is properly placed on the person's ear; "front" and "forward" refer to a direction towards the front of a person's head from a given point when the articulating ear shield is properly placed on the person's ear; "top," "upward," and "upper" refer to a direction towards a top of a person's head from a given point when the articulating ear shield is properly placed on the person's ear; and "bottom," "lower," and "downward" refer to a direction towards a bottom of a person's head from a given point when the articulating ear shield is properly placed on the person's ear.

Figure 12:
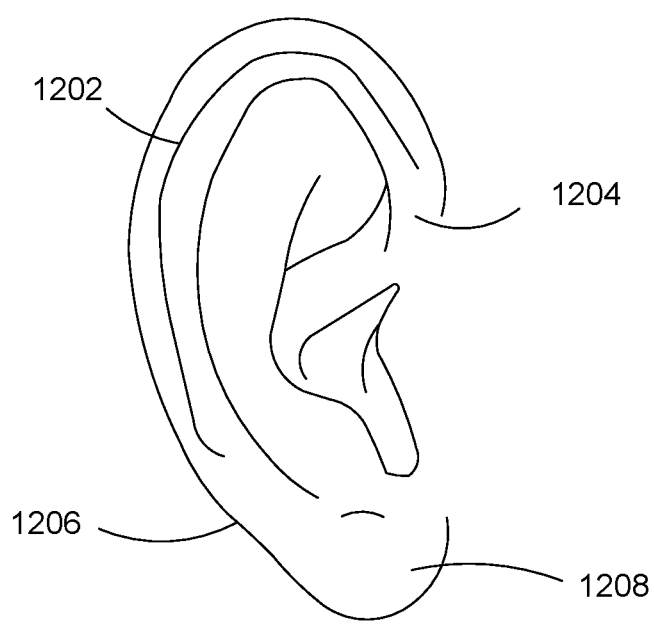
FIG. 12 shows the auricle of the external portion of a human ear, for reference.

FIG. 12 show the auricle 1200 of the external or outer portion of a human ear. In particular, the lateral side of the auricle is shown, and the medial side is on the opposite side of the auricle, facing the person's head. The auricle includes a helix 1202, which starts at the crus of helix 1204 and traverses upward to form the top of the auricle, and down the rear of the auricle to the helical tail 1206 where it meets the lobule or ear lobe 1208.

Figure 10:
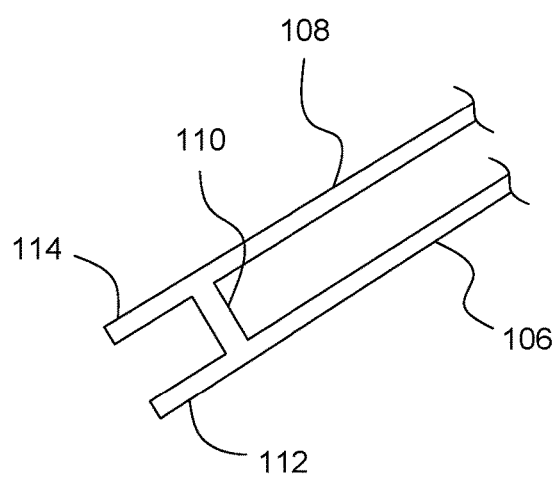
FIG. 10 is a top view of a support structure for an articulated ear shield in a neutral position, in accordance with some embodiments.

The articulated ear shield 100 is comprised of a support structure 102 and a heat resistant pliable cover 104. The support structure 102 supports the cover 104, and is comprised of a relatively stiff, although not necessarily inflexible, material. The support structure 102 includes two major portions that go over and behind a wearer's ear, and specifically over and behind the auricle. The lateral portion 106 goes over the lateral (outward) side of the auricle (e.g 1200). The auricle is bounded around the top and rear by the helix (e.g. 1202), which traverses downward along the back of the auricle to the lobule, commonly referred to as the ear lobe (e.g. 1208). The medial portion 108 is positioned to be over the medial side of the auricle, can engage the medial surface of the auricle (e.g. along the eminence of the scapha). The lateral portion 106 and the medial portion 108 are joined by a joining portion 110, which is between the lateral portion 106 and the medial portion 108, in a direction perpendicular to the page in FIGS. 1 and 2. The joining portion 110 allows the lateral portion 106 and the medial portion 108 to move, relative to each other, and biases the lateral portion 106 and medial portion 108 to a neutral position with respect to each other, as shown, for example, in FIG. 10, acting as a cantilevered spring member. The neutral position can be with the lateral and medial portions substantially parallel to each other. The joining portion 110, medial portion 108, and lateral portion 106 can be formed together as unitary polymeric structure. That is, a one-piece unit that is molded in a polymeric material such as plastic.

The heat resistant pliable cover 104 covers the outside or outer surface of the lateral portion 106 and an outside of the medial portion 108, and extends outward around the lateral portion 106 in a plane defined by the lateral portion 106, turning toward the medial side of the auricle (when worn) around a portion of the perimeter of the heat resistant pliable cover 104 around the lateral portion 106 in a configuration to cover the helix and a lobule of the auricle. The heat resistant pliable cover 104 can cover the entirety of the auricle, or a portion thereof.

Figure 11:
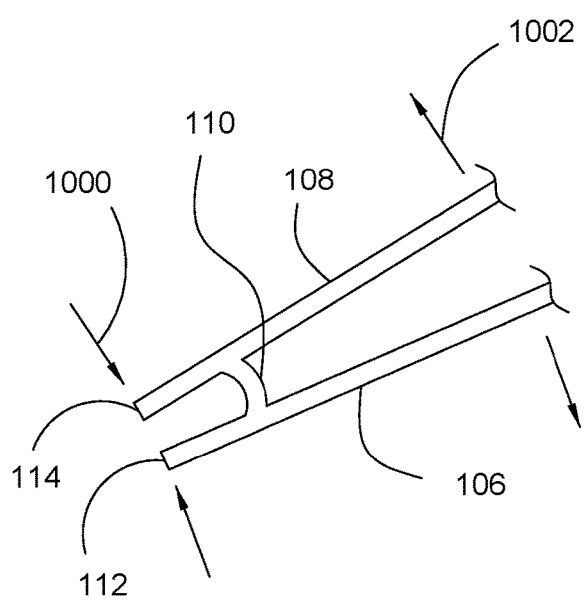
FIG. 11 is a top view of a support structure for an articulated ear shield in an opened position, in accordance with some embodiments.

To facilitate moving the lateral and medial portions, 106, 108, a person can squeeze the lateral articulating tab 112 and the medial articulating tab 114 towards each other, and shown, for example, in FIG. 11. The lateral articulating tab 112 extends to the rear of the joining portion 110 at the lateral side, opposite the lateral portion, and the medial articulating tab extends to the rear of the joining portion 110 from the medial side, defining a vertical trough or void 116 bounded by the joining portion 110, lateral articulating tab 112, and medial articulating tab 114. The void 116 extends above and below the joining section 110 and articulating tabs 112, 114, as seen in FIG. 3, by the exclusion of the material of the cover 104 from these areas. Thus, by moving ("squeezing") the lateral and medial articulating tabs 112, 114 towards each other (e.g. as indicated by arrows 1000 in FIG. 11), the lateral and medial portions 106, 108 move apart, at an angle (e.g. as indicated by arrows 1002 in FIG. 11), with the lateral and medial portions being fixed at the joining portion 110, which acts as a cantilevered spring, being deflected from its neutral position and then returning to its neutral position when the force at the articulating tabs 112, 114 is removed. As the lateral and medial articulating tabs 112, 114 are moved towards each other, the farther forward from the joining portion 110, the farther apart the corresponding points on the lateral and medial portions will be from each other. By utilizing the joining portion 110 as a cantilevered member, with the support structure 102 as a unitary member, there are no gaps that could pinch the user's ear, as with conventional springs or other separate clip portions moving relative to each other.

Thus, the lateral and medial articulating tabs 112, 114 can be moved together to open the articulating ear shield for placement of the articulating ear shield on a person's ear. Once in place, the user can release the lateral and medial articulating tabs 112, 114, allowing the lateral and medial portions 106, 108 to move back towards the neutral position, as biased by the joining portion 110. The separation between the lateral and medial portions 106, 108 can be designed such that the neutral position is less than the thickness of an average thickness of a human auricle, resulting in some pressure being applied to the auricle from the lateral and medial portions 106, 108 being biased together, which can aid in retaining the articulating ear shield 100 on the auricle.

The cover 104 can be made of any of several heat insulating, pliable materials, such as, for example, silicone rubber. In some embodiments the cover 104 can be optically translucent or near-transparent, and in some embodiments the cover 104 can be optically opaque. In embodiments where the cover 104 is translucent, the material of the support structure 102 can be made in a variety of colors so that users can pick a preferred color.

The lateral portion 106 of the support structure 102 extends forward from the joining portion 110 at a lateral side of the joining portion 110 and defines a lateral plane, and is configured to fit over a lateral side of the auricle. Similarly, the medial portion 108 extends upward and forward from a medial side of the joining portion 110 and defines a medial plane, and is configured to fit over a medial side (or a portion of the medial side) of the auricle. This means that the lateral portion 106 and the medial portion 108 are substantially planar, and most or all of these respective portions 106, 108 are substantially within their respective planes. When in the neutral position, the lateral and medial planes can be substantially parallel in some embodiments.

The lateral and medial portions 106, 108 of the support structure 102 oppose each other with respect to the joining portion 110, and together form a general "butterfly" shape. That is, each of the portions 106, 108 have an upper lobe that extends forward and upward from the joining section 110, and a lower lobe that extends forward and downward from the joining section 110. Accordingly, there is a lateral upper lobe 118, a lateral lower lobe 120, a medial upper lobe 122 and a medial lower lobe 124. The lower lobes 120, 124 are extended (i.e. longer) relative to the upper lobes 118, 122, in accordance with the general shape of the auricle, and the upper and lower lobes one each side form a general arc or arcuate shape. The lobes 118, 120 of the lateral portion 106 are wider (i.e. extend farther forward from the joining portion) than the lobes 122, 124 of the medial portion 108 as the lateral portion 106 covers substantially the entire auricle, while the medial portion 108 is configured to span the medial side of the helix of the auricle down to the medial side of the lobule.

The cover 104 is formed over the lateral and medial portions 106, 108, and extends outward from the lateral and medial portions 106, 108 in the lateral and medial planes defined by the lateral and medial portions 106, 108. The material of the cover 104 can also extend over the lateral and medial articulating tabs 112, 114 as well. In some embodiments the cover 104 can be molded over ("overmolded") the support structure 102, which can be provided as a unitary member, formed by molding a plastic or polymeric material suitably stiff for the application. Along a major part of the perimeter of the cover 104 on the lateral portion 106 side, the cover is turned or curved inward, toward the medial portion, forming a rim 126 that extends over the helix and lobule of the auricle.

Thus, the support structure 102 and cover 104 form a pocket or space inside the articulated ear shield 100 in which substantially the entire auricle of a person's ear can fit. The articulated ear shield 100 can be opened by pressing the articulating tabs 112, 114 together to allow the articulating ear shield to be placed on and over the auricle of a person's ear. A tactile protrusion 130 can be provided to allow a user to grip at the proper location to squeeze the articulating tabs 112, 114 towards each other. Once the articulating tabs 112, 114 are released, a portion of the auricle can be captured between the lateral portion 106 and the medial portion 108 to retain the articulated ear shield on the auricle. The geometry of the lateral portion 106, medial portion 108, and joining portion 110 can be designed so that any force against the wearer's ear is minimal, and not uncomfortable. Designers can take advantage of the fact that the helix and lobule of the auricle are generally not as sensitive to pressure as other portions of the body.

In order to provide ventilation and improve the ability to hear when wearing the articulated ear shield, one or more openings 128 can be provided through the cover 104 and the lateral portion 106.

Figure 9:
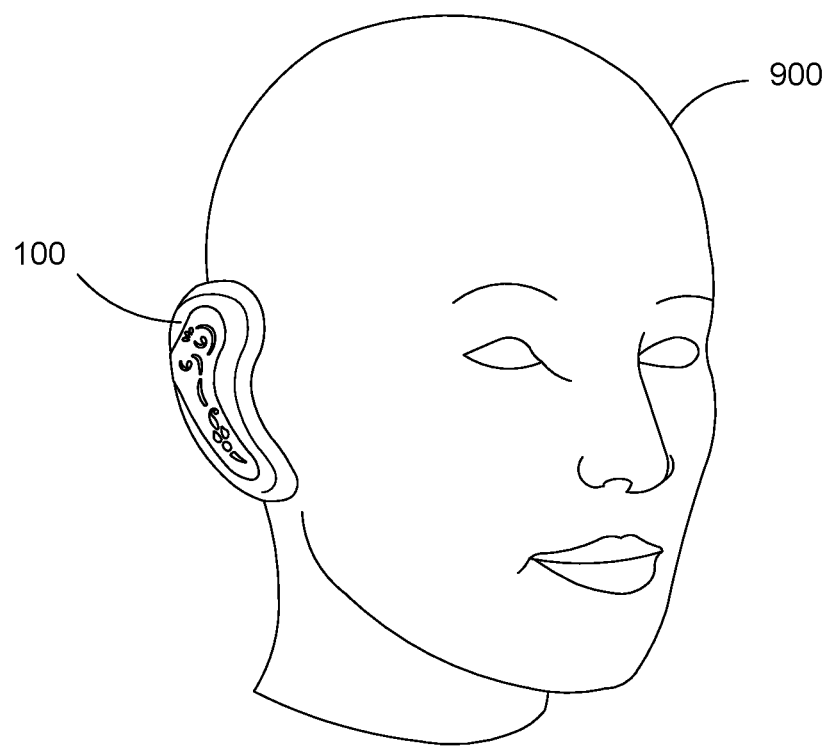
FIG. 9 is a perspective view of a person wearing an articulated ear shield, in accordance with some embodiments.

FIG. 9 is a perspective view of a person 900 wearing an articulated ear shield, in accordance with some embodiments. The lateral portion fits over a major portion of the auricle, particularly the helix and lobule, and the cover extends from the lateral portion so that the rim at the perimeter of the cover on the lateral side can extend over the helix and lobule, and the rest of the auricle, in the direction of the medial side to completely cover the outer ear. The medial portion and cover on the medial side can bear against the medial side of the helix to retain the articulated ear shield on the outer ear of the person 900. Although the right ear is shown here, and the articulated ear shield 100 is configured for the right ear, it will be appreciated that an articulated ear shield for the left ear can be readily designed form the disclosure herein, as a mirror image of the right articulating ear shield.

The disclosed articulated ear shield protects a wearer's ears from sharp, and/or hot instruments, as well as chemicals, while, for example, having their hair styled. The disclosed ear shields provide a vast improvement over known ear protection because of the articulating function of the ear shield structure, allowing a person to essentially "clip" an ear shield onto their ear by opening the lateral and medial portion apart from each other, placing the ear shield over the ear, and then releasing the articulating tabs to allow the lateral and medial portions to move back together, as biased by the joining member. This structure offers improved retention on the ear over known ear shields that simply hang on a user's ear, with no ability to retain itself on ear, and often falling off. Furthermore, the compliant cover provides a more comfortable experience than prior hard shell ear shields.

What is claimed is:

1. An ear shield for covering an auricle of a human ear, comprising:
   a support structure including a medial portion and a lateral portion integrally joined by a joining portion in the ear shield that is configured to be positioned at a rear of the auricle when the ear shield is placed on a human ear, the lateral portion and medial portion being configured to receive a helix and lobule of the auricle therebetween;
   the medial portion extending forward from the joining portion at a medial side of the joining portion and defining a medial plane, and being configured to fit over a medial side of the auricle;
   the lateral portion extending forward from the joining portion at a lateral side of the joining portion and defining a lateral plane, and being configured to fit over a lateral side of the auricle;
   a medial articulating tab extending rearward from the joining portion at the medial side of the joining portion;
   a lateral articulating tab extending rearward from the joining portion at the lateral side of the joining portion;
   the joining portion being configured to have a cantilevered spring action that biases the medial portion and the lateral portion to a neutral position with respect to each other in which the medial portion and lateral portion are separated by a space between the medial portion and the lateral portion, and the medial plane and lateral plane are substantially parallel, and wherein the joining portion is substantially perpendicular to both the medial plane and the lateral plane when the medial portion and the lateral portion are in the neutral position;
   wherein the medial portion, lateral portion, medial articulating tab, lateral articulating tab, and joining portion are a unitary polymeric structure;
   a pliable heat resistant cover disposed over an outer surface the lateral portion and over an outer surface of the medial portion, and which extends outward from the lateral portion in the lateral plane around at least a portion of a perimeter of the lateral portion, the pliable heat resistant cover forms a rim that curves inward from the lateral portion to a position over a top of the medial portion so as to cover the space between the lateral portion and the medial portion; and wherein the articulating ear shield is configured exclusively to be worn on one of either a left ear or a right ear.

2. The ear shield of claim 1, further comprising a plurality of openings formed through the lateral portion of the support structure and the pliable heat resistant cover over the lateral portion.

3. The ear shield of claim 1, wherein the pliable heat resistant cover is silicone rubber.

4. The ear shield of claim 1, wherein the joining portion, medial portion, lateral portion, medial articulating tab, and lateral articulating tab are integrally formed as a unitary polymeric structure.

5. The ear shield of claim 1, wherein the lateral portion and the pliable heat resistant cover on the lateral portion is further configured to cover an entirety of the lateral side of the auricle.

6. The ear shield of claim 1, wherein the pliable heat resistant cover extends over the medial articulating tab and the lateral articulating tab, and defines a void between the medial articulating tab and the lateral articulating tab, forming a vertical trough.

7. The ear shield of claim 1, wherein:
the medial portion comprises an upper lobe that extends upward and forward from the joining portion, and a lower lobe that extends downward and forward from the joining portion, and wherein the upper lobe and the lower lobe of the medial portion form a generally arcuate shape, and wherein the lower lobe extends farther forward than the upper lobe of the medial portion;
the lateral portion comprises an upper lobe that extends upwards and forwards from the joining portion, and a lower lobe that extends downward and forward from the joining portion, and wherein the upper lobe and the lower lobe of the lateral portion form a generally arcuate shape, and wherein the lower lobe extends farther forward than the upper lobe of the lateral portion; and
wherein the upper lobe of the medial portion extends above the upper lobe of the lateral portion, and the upper and lower lobes of the lateral portion both extend farther forward than the upper and lower lobes of the medial portion.

8. The ear shield of claim 1, further comprising a tactile protrusion formed on the heat resistant pliable cover over the lateral articulating tab.

9. An articulating ear shield for preventing exposure of a person's ear to styling implements and chemicals, comprising:
a support structure having a lateral portion and a medial portion joined by a joining portion that is a cantilevered spring member between the lateral portion and the medial portion, the joining portion being configured to bias the lateral portion and the medial portion to a neutral position relative to each other, wherein in the neutral position a lateral plane defined by the lateral portion and a medial plane defined by the medial portion are substantially parallel and the lateral portion and medial portion are separated defining a space between them, the lateral portion configured to engage a lateral side of the auricle, the medial portion configured to engage a medial side of the auricle along a helix of the auricle;

the support structure further including a lateral articulating tab extending from the joining portion at a lateral side of the joining portion in an opposite direction from which the lateral portion extends;

the support structure further including a medial articulating tab extending from the joining portion at a medial side of the joining portion in an opposite direction from which the medial portion extends;

wherein the medial portion, lateral portion, medial articulating tab, lateral articulating tab, and joining portion are a unitary polymeric structure;

a heat resistant pliable cover disposed over, and which covers, an outside of the lateral portion and an outside of the medial portion, and which further covers and is disposed over the lateral articulating tab and the medial articulating tab, and which extends outward from the lateral articulating tab and around the lateral portion of the support structure in a plane defined by the lateral portion, and which forms a rim that curves inward from the lateral plane to a position over a top of the medial portion so as to cover the space between the lateral portion and the medial portion, the rim forming a portion of a perimeter of the heat resistant pliable cover on the lateral portion in a configuration to cover the helix and a lobule of the auricle; and wherein the articulating ear shield is configured exclusively to be worn on either a left ear or a right ear.

10. The articulating ear shield of claim 9, further comprising a plurality of openings formed through the lateral portion of the support structure and the pliable heat resistant cover over the lateral portion.

11. The articulating ear shield of claim 9, wherein the pliable heat resistant cover is silicone rubber.

12. The articulating ear shield of claim 9, wherein:
the medial portion comprises an upper lobe that extends upward and forward from the joining portion, and a lower lobe that extends downward and forward from the joining portion, and wherein the upper lobe and the lower lobe of the medial portion form a generally arcuate shape, and wherein the lower lobe extends farther forward than the upper lobe of the medial portion;
the lateral portion comprises an upper lobe that extends upwards and forwards from the joining portion, and a lower lobe that extends downward and forward from the joining portion, and wherein the upper lobe and the lower lobe of the lateral portion form a generally arcuate shape, and wherein the lower lobe extends farther forward than the upper lobe of the lateral portion; and
wherein the upper lobe of the medial portion extends above the upper lobe of the lateral portion, and the upper and lower lobes of the lateral portion both extend farther forward than the upper and lower lobes of the medial portion.

13. The articulating ear shield of claim 9, further comprising a tactile protrusion formed on the heat resistant pliable cover over the lateral articulating tab.

14. The articulating ear shield of claim 9, wherein the pliable heat resistant cover extends over the medial articulating tab and the lateral articulating tab, and defines a void between the medial articulating tab and the lateral articulating tab, forming a vertical trough.

15. The articulating ear shield of claim 9, wherein the heat resistant pliable cover is overmolded onto the support structure.

16. An articulating ear shield for protecting an auricle of a human ear, comprising:
- a support structure having a lateral portion and a medial portion which are joined together by a joining portion, and which are spaced apart from each other by the joining portion, thereby defining a space in a configuration to receive the auricle between the lateral portion and the medial portion, wherein the lateral portion extends forward from the joining portion at a lateral side of the joining portion, the medial portion extends forward from the joining portion at a medial side of the joining portion, and wherein the lateral portion is configured to fit over a lateral side of the human ear and the medial portion is configured to fit over the medial side of the human ear when the articulating ear shield is worn on the human ear, and wherein the articulating ear shield is configured exclusively to be worn on either a left ear or a right ear;
- a lateral articulating tab that extends to a rear from the joining portion at the lateral side of the joining portion;
- a medial articulating tab that extends to the rear from the joining portion at the medial side of the joining portion;
- a heat resistant pliable cover disposed over an outside of the lateral portion and an outside of the medial portion, and which extends outward over the lateral portion in a lateral plane defined by the lateral portion, and which, at a perimeter of the heat resistance pliable cover, forms a rim that curves inward to a position over a top of the medial portion so as to cover the space between the lateral portion and the medial portion, the rim being in a configuration to cover a helix and a lobule of the auricle;
- wherein the medial portion, lateral portion, medial articulating tab, lateral articulating tab, and joining portion are a unitary polymeric structure; and
- wherein the joining portion is a cantilevered spring member that biases the lateral portion and the medial portion to a neutral position where the lateral portion and the medial portion are separated and the lateral plane and a medial plane defined by the medial portion are substantially parallel, and wherein urging the lateral articulating tab and the medial articulating tab together causes the joining portion to flex and causes the lateral and medial portions to move apart at an angle.

17. The articulating ear shield of claim 16, wherein:

the medial portion comprises an upper lobe that extends upward and forward from the joining portion, and a lower lobe that extends downward and forward from the joining portion, and wherein the upper lobe and the lower lobe of the medial portion form a generally arcuate shape, and wherein the lower lobe extends farther forward than the upper lobe of the medial portion;

the lateral portion comprises an upper lobe that extends upwards and forwards from the joining portion, and a lower lobe that extends downward and forward from the joining portion, and wherein the upper lobe and the lower lobe of the lateral portion form a generally arcuate shape, and wherein the lower lobe extends farther forward than the upper lobe of the lateral portion; and wherein the upper lobe of the medial portion extends above the upper lobe of the lateral portion, and the upper and lower lobes of the lateral portion both extend farther forward than the upper and lower lobes of the medial portion.

18. The articulating ear shield of claim 16, further comprising a plurality of openings formed through the lateral portion of the support structure and the pliable heat resistant cover over the lateral portion.

19. The articulating ear shield of claim 16, wherein the pliable heat resistant cover is silicone rubber.

* * * * *